(12) United States Patent
Sudo et al.

(10) Patent No.: US 9,635,341 B2
(45) Date of Patent: Apr. 25, 2017

(54) VIDEO PROCESSOR AND ACTIVATION METHOD OF VIDEO PROCESSOR

(71) Applicant: OLYMPUS CORPORATION, Tokyo (JP)

(72) Inventors: Masaru Sudo, Hachioji (JP); Kentaro Hase, Hachioji (JP); Masahito Yokouchi, Hachioji (JP); Hitoshi Komine, Hachioji (JP); Hidetaro Kono, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/286,079

(22) Filed: Oct. 5, 2016

(65) Prior Publication Data

US 2017/0039454 A1    Feb. 9, 2017

Related U.S. Application Data

(63) Continuation of application No. PCT/JP2015/061635, filed on Apr. 15, 2015.

(30) Foreign Application Priority Data

May 8, 2014 (JP) ................................ 2014-097062

(51) Int. Cl.
*H04N 13/00* (2006.01)
*G06K 9/62* (2006.01)
*G06T 15/00* (2011.01)

(52) U.S. Cl.
CPC ......... *H04N 13/004* (2013.01); *G06K 9/6267* (2013.01); *G06T 15/00* (2013.01);
(Continued)

(58) Field of Classification Search
CPC .. G06K 9/6267; G06K 2209/40; G06T 7/004; G06T 11/206; G06T 13/20; G06T 15/00;
(Continued)

(56) References Cited

U.S. PATENT DOCUMENTS 5,784,097 A * 7/1998 Iinuma ................... G06T 15/00
                                                    348/42
5,850,352 A * 12/1998 Moezzi .................. H04N 5/222
                                                    345/419

(Continued)

FOREIGN PATENT DOCUMENTS

EP          2360931 A1     8/2011
JP       2004-186863 A     7/2004
(Continued)

OTHER PUBLICATIONS

International Search Report dated Jul. 14, 2015 issued in PCT/JP2015/061635.
(Continued)

*Primary Examiner* — Manav Seth
(74) *Attorney, Agent, or Firm* — Scully, Scott, Murphy & Presser, P.C.

(57) ABSTRACT

A video processor includes: a judgement section configured to judge whether an input is a 2D or 3D image signal; an LR synthesis section configured to embed left and right image signals into an image signal in a side-by-side format to output the signal if the input is the 3D image signal and configured to embed a 2D image signal into a position corresponding to one of the left and right in an image signal in a side-by-side format to output the signal if the input is the 2D image signal; and an image processing section configured to apply image processing to the image signal in the side-by-side format.

6 Claims, 6 Drawing Sheets

(52) U.S. Cl.
CPC ..... *H04N 13/0007* (2013.01); *H04N 13/0029* (2013.01); *H04N 13/0051* (2013.01); *G05B 2219/23167* (2013.01); *G06T 2207/10136* (2013.01); *H04N 2013/0096* (2013.01)

(58) Field of Classification Search
CPC .......... G06T 15/08; G06T 2207/10136; G05B 2219/23167; H04N 13/0007; H04N 13/0029; H04N 13/004; H04N 13/0051; H04N 13/0055; H04N 2013/0096
See application file for complete search history.

(56) References Cited

U.S. PATENT DOCUMENTS

| | | | | |
|---|---|---|---|---|
| 6,445,814 | B2* | 9/2002 | Iijima | H04N 13/0022 348/46 |
| 6,823,080 | B2* | 11/2004 | Iijima | H04N 13/0022 348/42 |
| 6,862,364 | B1* | 3/2005 | Berestov | G06T 5/008 345/426 |
| 7,636,088 | B2* | 12/2009 | Nomura | H04N 13/0022 345/419 |
| 8,570,362 | B2* | 10/2013 | Park | H04N 13/0029 345/428 |
| 8,625,970 | B2* | 1/2014 | Toma | H04N 13/0055 348/43 |
| 2004/0145655 | A1 | 7/2004 | Tomita | |
| 2010/0231593 | A1* | 9/2010 | Zhou | G06T 3/4007 345/428 |
| 2011/0187818 | A1 | 8/2011 | Hasegawa et al. | |
| 2011/0242370 | A1 | 10/2011 | Endo | |
| 2012/0188338 | A1 | 7/2012 | Fukuyama | |
| 2013/0286243 | A1 | 10/2013 | Endo | |
| 2013/0286258 | A1 | 10/2013 | Endo | |
| 2014/0267857 | A1 | 9/2014 | Endo | |
| 2015/0062295 | A1* | 3/2015 | Yoneda | H04N 13/0029 348/43 |
| 2016/0133014 | A1* | 5/2016 | Staples, II | G06T 7/248 382/103 |

FOREIGN PATENT DOCUMENTS

| | | |
|---|---|---|
| JP | 2011-087088 A | 4/2011 |
| JP | 2011-160020 A | 8/2011 |
| JP | 2011-216948 A | 10/2011 |
| WO | WO 2011/045872 A1 | 4/2011 |
| WO | WO 2013/031156 A1 | 3/2013 |
| WO | WO 2014/050447 A1 | 4/2014 |

OTHER PUBLICATIONS

Japanese Office Action dated Dec. 15, 2015 issued in JP 2015-551301.

* cited by examiner

FIG. 3

```
4400x1125i(59.94Hz)/5280x1125i(50Hz)
┌─────────────────────────┬─────────────────────────┐
│                         │                         │
│      1920x1080i         │      1920x1080i         │
│   (L IMAGE/2D IMAGE)    │       (R IMAGE)         │
│                         │                         │
└─────────────────────────┴─────────────────────────┘
```

1920x1080p

VIDEO PROCESSOR AND ACTIVATION METHOD OF VIDEO PROCESSOR

CROSS REFERENCE TO RELATED APPLICATION

This application is a continuation application of PCT/JP2015/061635 filed on Apr. 15, 2015 and claims benefit of Japanese Application No. 2014-097062 filed in Japan on May 8, 2014, the entire contents of which are incorporated herein by this reference.

BACKGROUND OF INVENTION

1. Field of the Invention

The present invention relates to a video processor configured to apply image processing to a 3D image signal including a left image signal and a right image signal and an activation method of the video processor.

2. Description of the Related Art

In recent years, a 3D endoscope capable of stereoscopic observation has been proposed and manufactured. An example of configuration of a video processor configured to process a 3D image signal including a left image signal and a right image signal obtained from the 3D endoscope will be described with reference to FIG. 6.

FIG. 6 is a block diagram showing an example of configuration of a conventional video processor configured to display a 3D image signal.

In the example of configuration shown in FIG. 6, one 2D video processor 90L processes a left image signal L obtained from the 3D endoscope, and another 2D video processor 90R processes a right image signal R. A 3D synthesis section 99 synthesizes the processed left image signal and right image signal to perform 3D display.

A 3D image signal is basically picked up at a high definition (HD: high definition), and the left image signal L and the right image signal R are inputted at an HD clock (for example, 74 MHz). There is no difference between internal structures of the 2D video processor 90L configured to apply image processing to the inputted left image signal L and the 2D video processor 90R configured to apply image processing to the inputted right image signal R, and the 2D video processors 90L and 90R are normal video processors capable of processing high definition (HD) 2D image signals.

That is, each of the 2D video processors 90L and 90R includes: a connection portion 91 for connecting an endoscope; a clock changing section 92 configured to convert a clock of an image signal to a clock for executing imaging processing or the like; an image processing section 93 configured to execute image processing; an HD resolution conversion section 94 configured to convert a resolution of an image signal to a resolution of an HD image signal; a clock changing section 95 configured to convert a clock of an image signal to a standard definition (SD: standard definition) clock (for example, 13.5 MHz); an SD resolution conversion section 96 configured to convert a resolution of an image signal to a resolution of an SD image signal; an HD enhancement section 97 configured to apply an enhancement processing to an HD image signal; and an SD enhancement section 98 configured to apply an enhancement processing to an SD image signal.

When the 2D video processor 90L or 90R operates alone, a 2D HD endoscope is connected to input a 2D-HD image signal, or an SD endoscope (SD endoscope is basically only for 2D) is connected to input an SD image signal. In the 2D video processor 90L or 90R, the image processing section 93 executes the image processing at an HD clock to allow handling an HD image signal. Therefore, the clock changing section 92 changes the SD clock to the HD clock when an SD image signal is inputted and does not particularly change the clock when an HD image signal is inputted. To output the HD image signal to an HD monitor, the HD resolution conversion section 94 and the HD enhancement section 97 process the image signal subjected to the image processing by the image processing section 93. On the other hand, to output the SD image signal to an SD monitor, the clock changing section 95 changes the clock to the SD clock, and the SD resolution conversion section 96 and the SD enhancement section 98 process the image signal subjected to the image processing by the image processing section 93. Here, the 2D video processor 90L or 90R can perform both of outputting the HD image signal to the HD monitor and outputting the SD image signal to the SD monitor regardless of whether the input image signal is a 2D-HD image signal or an SD image signal.

When the 2D video processors 90L and 90R are combined to execute processing of a 3D-HD image signal by connecting a 3D-HD endoscope, the 2D video processor 90L can process the left image signal L, and the 2D video processor 90R can process the right image signal R. The 3D synthesis section 99 can perform 3D synthesis of the left image signal L outputted form the HD enhancement section 97 of the 2D video processor 90L and the right image signal R outputted from the HD enhancement section 97 of the 2D video processor 90R, and a 3D image signal can be displayed on a 3D-HD monitor. Even when a 3D-HD image signal is inputted, an output from one of the HD enhancement sections 97 can be connected to the HD monitor to observe one of the left image signal L and the right image signal R as a 2D HD image signal, and an output from one of the SD enhancement sections 98 can be connected to an SD monitor to observe one of the left image signal L and the right image signal R as a 2D SD image signal.

SUMMARY OF THE INVENTION

An aspect of the present invention provides a video processor including: a judgement section configured to judge whether an inputted image signal is a 3D image signal including a left image signal and a right image signal or a 2D image signal; an image signal synthesis section configured to embed the left image signal and the right image signal into an image signal in a side-by-side format to output the signal if the judgement section judges that the inputted image signal is the 3D image signal and configured to embed the 2D image signal into a position corresponding to one of a left image and a right image in an image signal in a side-by-side format to output the signal if the judgement section judges that the inputted image signal is the 2D image signal; and an image processing section configured to apply image processing to the image signal in the side-by-side format outputted by the image signal synthesis section.

An aspect of the present invention provides an activation method of a video processor, the method including: by a judgement section, judging whether an inputted image signal is a 3D image signal including a left image signal and a right image signal or a 2D image signal; by an image signal synthesis section, embedding the left image signal and the right image signal into an image signal in a side-by-side format to output the signal if the judgement section judges that the inputted image signal is the 3D image signal and embedding the 2D image signal into a position corresponding to one of a left image and a right image in an image signal in a side-by-side format to output the signal if the judgement section judges that the inputted image signal is the 2D image signal; and by an image processing section, applying image processing to the image signal in the side-by-side format outputted by the image signal synthesis section.

BRIEF DESCRIPTION OF THE DRAWINGS

FIG. 3 is a diagram showing an example of image signals synthesized by an LR synthesis section according to the first embodiment;

FIG. 5 is a diagram showing an example of an HD image signal outputted from an HD resolution conversion section according to the second embodiment.

DETAILED DESCRIPTION OF THE PREFERRED EMBODIMENT(S)

Hereinafter, embodiments of the present invention will be described with reference to the drawings.

First Embodiment

Figure 1:
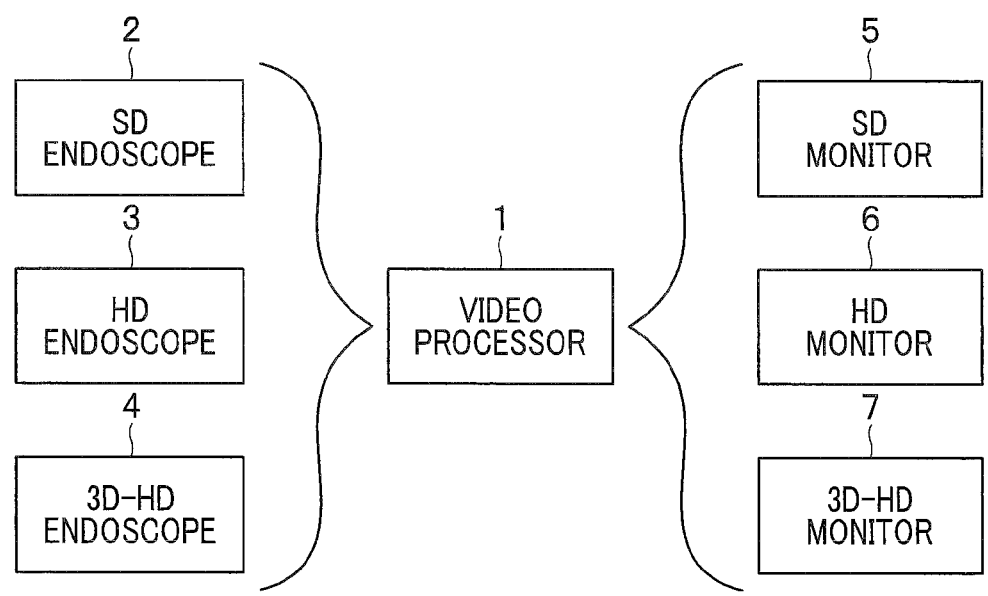
FIG. 1 is a block diagram showing a configuration of an endoscope system according to a first embodiment of the present invention.
Figure 2:
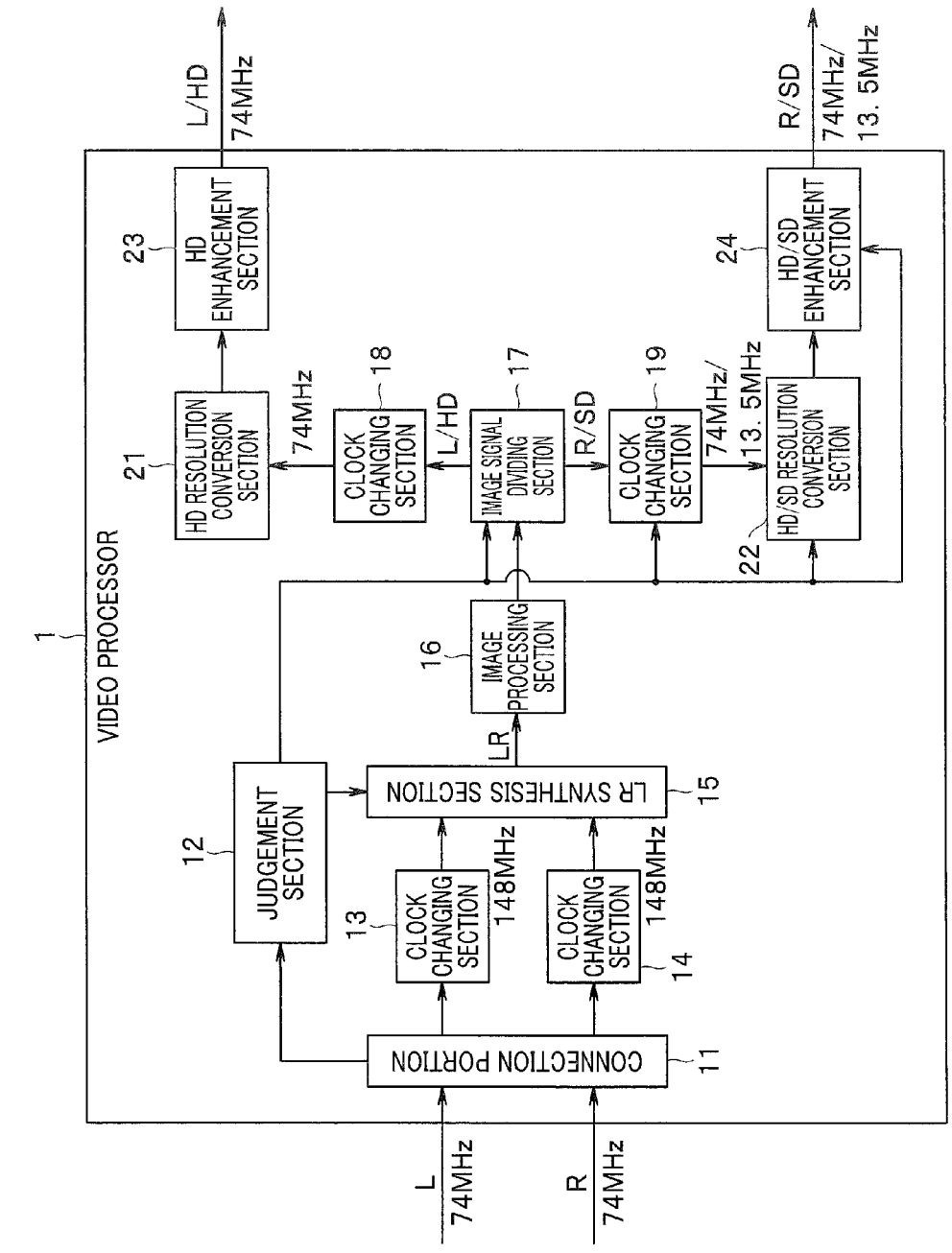
FIG. 2 is a block diagram showing a configuration of a video processor according to the first embodiment.

FIGS. 1 to 3 illustrate a first embodiment of the present invention, and FIG. 1 is a block diagram showing a configuration of an endoscope system.

The endoscope system includes a video processor 1 configured to execute image processing.

An SD endoscope 2 configured to pick up a standard definition (SD: standard definition) image signal (SD image signal), an HD endoscope 3 configured to pick up a 2D high definition (HD: high definition) image signal (HD image signal), and a 3D-HD endoscope 4 configured to pick up a 3D HD image signal (3D-HD image signal including a left image signal L and a right image signal R) can be selectively connected to the video processor 1. Here, since the SD image signal is only 2D, the SD image signal is a 2D-SD image signal, and the HD image signal denotes a 2D-HD image signal.

An SD monitor 5 configured to display an SD image signal, an HD monitor 6 configured to display an HD 2D image signal, and a 3D-HD monitor 7 configured to display a 3D-HD image signal can be connected to the video processor 1. Note that as long as 2D display and 3D display can be switched, a monitor may serve as both of the HD monitor 6 and the 3D-HD monitor 7. The SD monitor 5 and the HD monitor 6 may be connected to the video processor 1 at the same time.

Next, FIG. 2 is a block diagram showing a configuration of the video processor 1.

The video processor 1 includes a connection portion 11, a judgement section 12, a clock changing section 13, a clock changing section 14, an LR synthesis section 15, an image processing section 16, an image signal dividing section 17, a clock changing section 18, a clock changing section 19, an HD resolution conversion section 21, an HD/SD resolution conversion section 22, an HD enhancement section 23, and an HD/SD enhancement section 24.

One of the SD endoscope 2, the HD endoscope 3, and the 3D-HD endoscope 4 is selectively connected to the connection portion 11.

The judgement section 12 judges which one of the SD endoscope 2, the HD endoscope 3, and the 3D-HD endoscope 4 is connected to the connection portion 11 (therefore, which one of the 3D image signal including the left image signal L and the right image signal R and the 2D image signal is inputted) and outputs a judgement result indicating one of 2D connection (more specifically, SD connection or HD connection) or 3D connection (3D-HD connection).

The clock changing section 13 converts a clock of the image signal inputted through the connection portion 11 to a clock for executing image processing and the like. Here, the clock of the SD image signal is, for example, 13.5 MHz, and the clock of the HD image signal is, for example, 74 MHz regardless of whether the HD image signal is the 2D image signal, the left image signal L, or the right image signal R. On the other hand, the image processing section 16 according to the present embodiment is configured to operate at an image processing clock of 148 MHz that is twice as much as 74 MHz to allow processing both of the left image signal L and the right image signal R (therefore, to allow processing either one of the SD image signal and the 2D HD image signal with the number of pixels smaller than the number of pixels of the left image signal L and the right image signal R combined). Thus, the clock changing section 13 converts the clock to the image processing clock (for example, 148 MHz) regardless of whether the inputted image signal is the SD image signal, the 2D HD image signal, or the left image signal L.

Although the clock changing section 14 basically functions in the same way as the clock changing section 13, the 3D image signal is a 2-channel input of LR, and the 2D image signal is a 1-channel input. Therefore, assuming that the clock changing section 13 performs the clock changing of the 2D image signal, the clock changing section 14 converts the clock of the right image signal R to the image processing clock (for example, 148 MHz) only when the right image signal R is inputted.

When the judgement result of the judgement section 12 indicates the 3D connection (that is, when the inputted image signal is the 3D image signal), the LR synthesis section 15 synthesizes the left image signal L and the right image signal R and outputs a synthetic image signal (here, LR synthetic image signal). Here, FIG. 3 is a diagram showing an example of the image signal synthesized by the LR synthesis section 15. In the example shown in FIG. 3, the LR synthesis section 15 creates an LR synthetic image signal in a so-called side-by-side format with 4400×1125i (frame rate: 59.94 Hz) or 5280×1125i (frame rate: 50 Hz) from the left image signal L with 1920×1080i and the right image signal R with 1920×1080i (however, the LR synthetic image signal may be obviously created in another format).

On the other hand, when the judgement result of the judgement section 12 indicates the 2D connection (that is, when the inputted image signal is the 2D image signal (one of the SD image signal and the 2D HD image signal)), the LR synthesis section 15 embeds the inputted 2D image signal into one of the left image signal L and the right image signal R (for example, at a position corresponding to the left image signal L in FIG. 3) to create the synthetic image signal.

The image processing section 16 applies image processing to the synthetic image signal outputted from the LR synthesis section 15 at an image processing clock (for example, 148 MHz) twice or more than twice as much as the clock of the 3D image signal. The image processing appropriately includes general image processing, such as optical black subtraction processing, white balance processing, synchronization processing, noise removal processing, edge enhancement processing, and gamma conversion processing.

The image signal dividing section 17 divides the synthetic image signal subjected to the image processing into the left image signal L and the right image signal R.

That is, when the judgement result of the judgement section 12 indicates the 3D connection, the image signal dividing section 17 divides the LR synthetic image signal subjected to the image processing by the image processing section 16 into the left image signal L and the right image signal R. The image signal dividing section 17 outputs the left image signal L to the clock changing section 18 and outputs the right image signal R to the clock changing section 19.

When the judgement result of the judgement section 12 indicates the 2D connection, the image signal dividing section 17 divides the synthetic image signal subjected to the image processing by the image processing section 16 into the left image signal L and the right image signal R and outputs the left image signal L including one of the SD image signal and the 2D HD image signal to the clock changing section 18 and the clock changing section 19. In this case, the left image signal L outputted to the clock changing section 18 is outputted as an HD image signal in a later stage, and the left image signal L outputted to the clock changing section 19 is outputted as an SD image signal in a later stage.

The clock changing section 18 converts the clock of the image signal received from the image signal dividing section 17 from the image processing clock (for example, 148 MHz) to the HD clock (for example, 74 MHz).

On the other hand, the clock changing section 19 converts the image processing clock (for example, 148 MHz) of the image signal received from the image signal dividing section 17 to the HD clock (for example, 74 MHz) when the judgement result of the judgement section 12 indicates the 3D connection and converts the image processing clock to the SD clock (for example, 13.5 MHz) when the judgement result of the judgement section 12 indicates the 2D connection.

The HD resolution conversion section 21 converts a resolution of the image signal to a display resolution of one of the HD monitor 6 and the 3D-HD monitor 7 that are output monitors. A plurality of types of resolution, such as a full resolution and a resolution lower than the full resolution, may exist for the HD image signal. Therefore, the HD resolution conversion section 21 performs the resolution conversion not only when the input image signal is the SD image signal, but also performs the resolution conversion as necessary when the input image signal is the HD image signal.

In this way, the clock changing section 18 and the HD resolution conversion section 21 form a high definition conversion section configured to convert the resolution of one of the left image signal L and the right image signal R divided by the image signal dividing section 17 or the resolution of the 2D image signal embedded into the one of the left image signal L and the right image signal R (for example, left image signal L) to the resolution of the high definition image signal with the clock of the 3D image signal.

The HD/SD resolution conversion section 22 converts the resolution of the image signal to the display resolution of the 3D-HD monitor 7 that is the output monitor when the judgement result of the judgement section 12 indicates the 3D connection and converts the resolution of the image signal to the display resolution of the SD monitor 5 that is the output monitor when the judgement result of the judgement section 12 indicates the 2D connection.

In this way, the clock changing section 19 and the HD/SD resolution conversion section 22 form a standard definition conversion section configured to convert the resolution of the other of the left image signal L and the right image signal R divided by the image signal dividing section 17 to the resolution of the high definition image signal with the clock of the 3D image signal when the judgement section 12 judges that the signal is the 3D image signal and configured to convert the resolution of the 2D image signal embedded into the one of the left image signal L and the right image signal R (for example, left image signal L) to the resolution of the standard definition image with the clock of the standard definition image when the judgement section 12 judges that the signal is the 2D image signal.

The HD enhancement section 23 applies an enhancement processing for HD to the HD image signal outputted from the HD resolution conversion section 21.

The HD/SD enhancement section 24 applies an enhancement processing for HD to the HD image signal outputted from the HD/SD resolution conversion section 22 when the judgement result of the judgement section 12 indicates the 3D connection and applies an enhancement processing for SD to the SD image signal outputted from the HD/SD resolution conversion section 22 when the judgement result of the judgement section 12 is the 2D connection.

According to the video processor 1 with the configuration, a combination of the output from the HD enhancement section 23 and the output from the HD/SD enhancement section 24 is "left image signal L and right image signal R" in the 3D connection and is "HD image signal and SD image signal" in the 2D connection.

Figure 6:
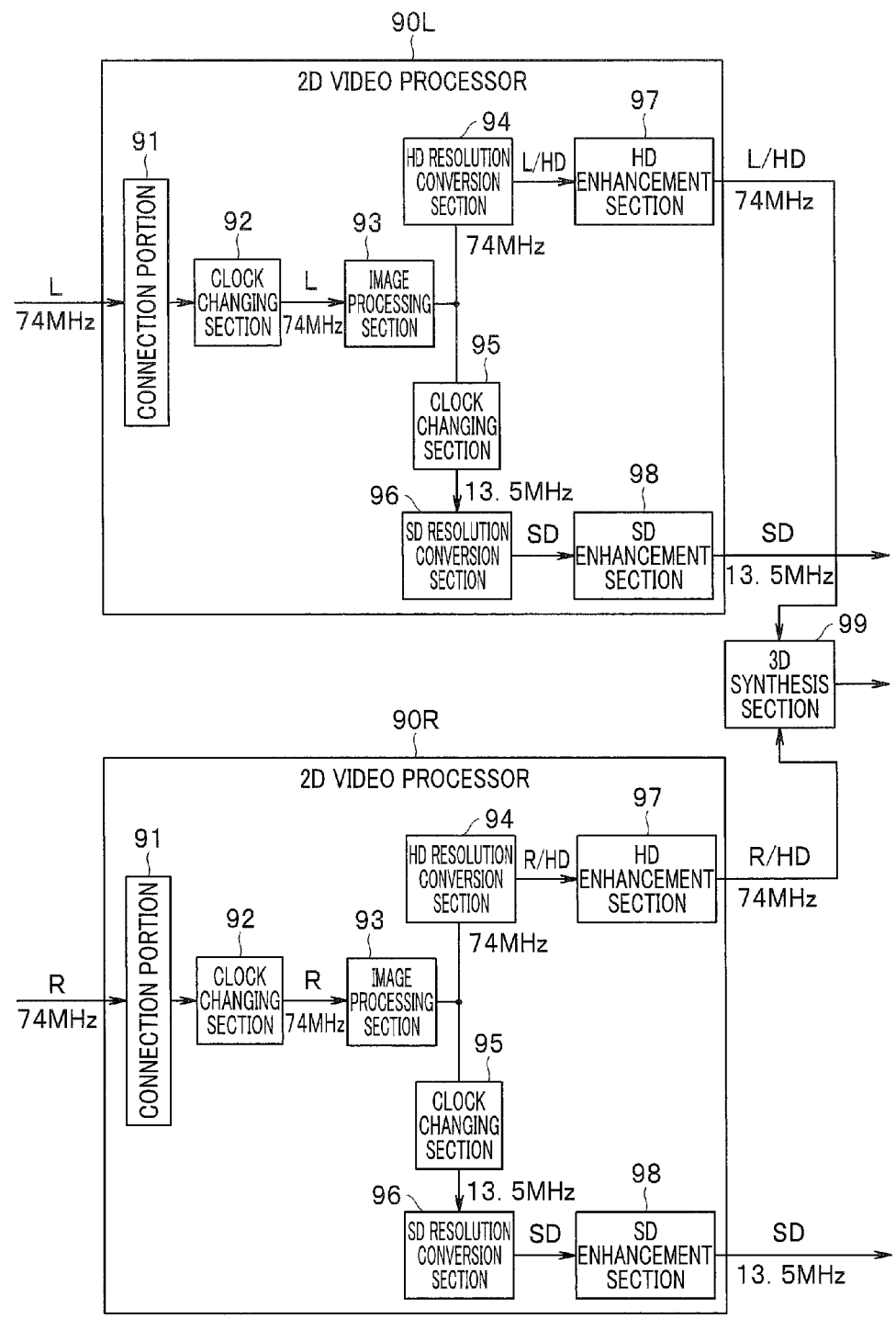
FIG. 6 is a block diagram showing an example of configuration of a conventional video processor configured to display a 3D image signal.

Although two image processing sections 93 for the left image signal L and the right image signal R are necessary to display the 3D image signal according to the conventional configuration shown in FIG. 6, the process can be executed by only one image processing section 16 according to the first embodiment. The configuration can be simple, and a video processor configured to process both of a 2D image signal and a 3D image signal can be inexpensively provided.

Although two video processors are necessary according to the conventional configuration shown in FIG. 6, one video processor is required according to the present embodiment. Therefore, the configuration of the endoscope system can be simplified, and the cost of the entire system can be reduced.

According to the conventional configuration shown in FIG. 6, there are outputs of four systems in total, outputs from two HD enhancement sections 97 and outputs from two SD enhancement sections 98. Therefore, when one of the SD endoscope 2, the HD endoscope 3, and the 3D-HD endoscope 4 is connected, some of the output systems may not be used. For example, when the 3D-HD endoscope 4 is connected, the output systems of two SD enhancement sections 98 are not used. When one of the SD endoscope 2 and the HD endoscope 3 is connected, the output system of one HD enhancement section 97 and the output system of one SD enhancement section 98 are not used. On the other hand, according to the configuration of the present embodiment, unnecessary output systems can be reduced.

In addition, one of the two 2D video processors 90L and 90R is not necessary when one of the SD endoscope 2 and the HD endoscope 3 is connected according to the conventional configuration shown in FIG. 6, and moreover, the connection of the 3D synthesis section 99 is not necessary. Therefore, the connection of the entire system needs to be changed between the connection of the 3D-HD endoscope 4 and the connection of one of the SD endoscope 2 and the HD endoscope 3. On the other hand, the burden of changing the connection can be reduced according to the configuration of the present embodiment.

Second Embodiment

Figure 4:
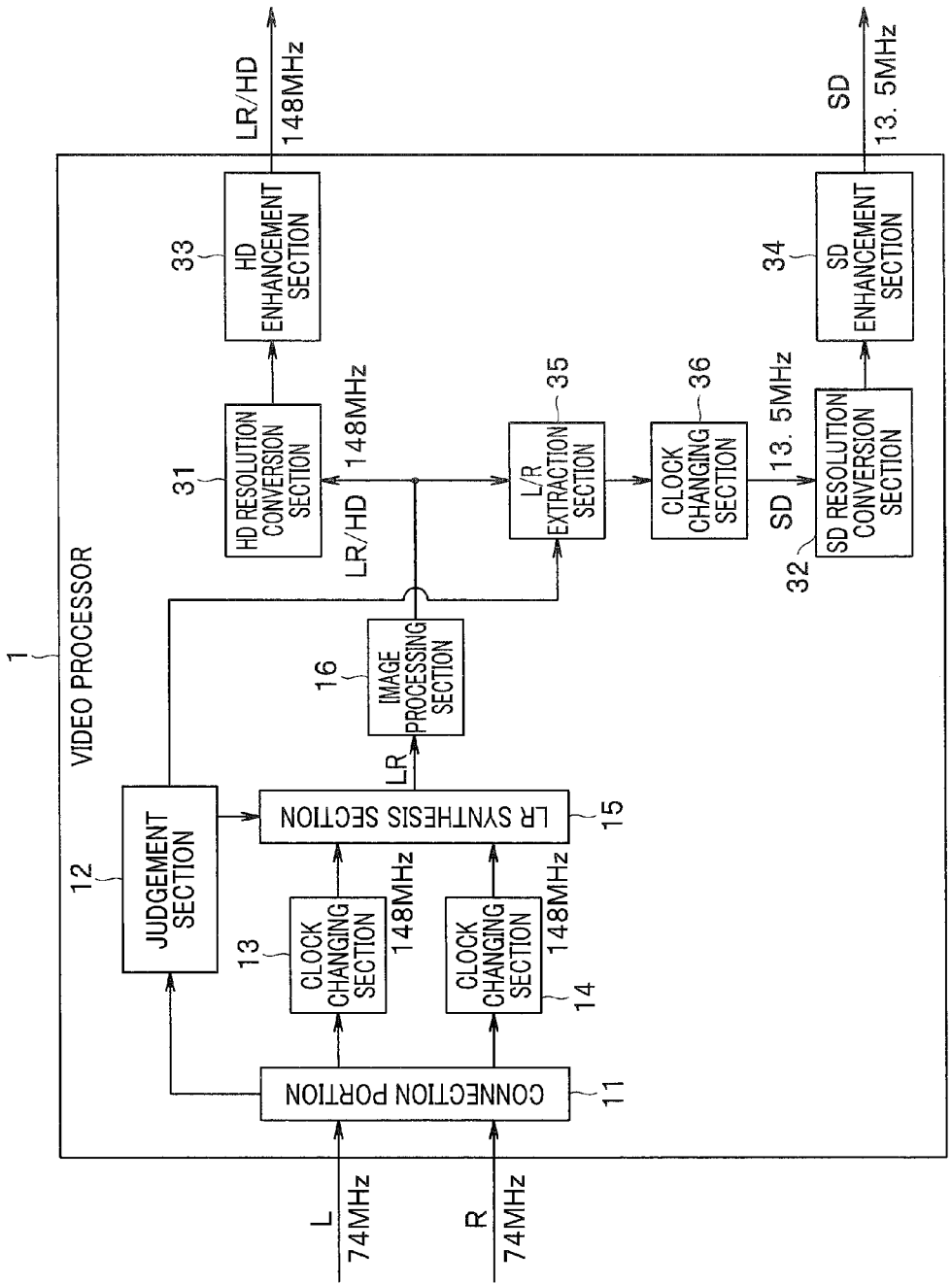
FIG. 4 is a block diagram showing a configuration of the video processor according to a second embodiment of the present invention.

FIGS. 4 and 5 illustrate a second embodiment of the present invention, and FIG. 4 is a block diagram showing a configuration of the video processor 1.

In the second embodiment, same reference signs are provided to same parts as those in the first embodiment, and the description will be appropriately omitted. Only differences will be mainly described.

In the first embodiment, the processing clock (for example, 148 MHz) is converted to the HD clock (for example, 74 MHz) to output the signal after the image processing when the input image signal is one of the 2D-HD image signal and the 3D-HD image signal. However, the present embodiment is an embodiment in which the signal is outputted without changing the processing clock.

The video processor 1 shown in FIG. 4 includes the connection portion 11, the judgement section 12, the clock changing section 13, the clock changing section 14, the LR synthesis section 15, the image processing section 16, an L/R extraction section 35, a clock changing section 36, an HD resolution conversion section 31, an SD resolution conversion section 32, an HD enhancement section 33, and an SD enhancement section 34.

Here, each configuration of the connection portion 11, the judgement section 12, the clock changing section 13, the clock changing section 14, the LR synthesis section 15, and the image processing section 16 is basically the same as those in the first embodiment.

The L/R extraction section 35 is an image signal extraction section configured to extract one of the left image signal L and the right image signal R from the LR synthetic image signal subjected to the image processing when the judgement section 12 judges that the signal is the 3D image signal and configured to extract one of the left image signal L and the right image signal R (for example, left image signal L) into which the 2D image signal is embedded and subjected to the image processing when the judgement section 12 judges that the signal is the 2D image signal.

That is, the L/R extraction section 35 extracts one of the left image signal L and the right image signal R (for example, left image signal L) from the synthetic image signal outputted from the image processing section 16 when the judgement result of the judgement section 12 indicates the 3D connection (when the 3D-HD endoscope 4 is connected) and extracts the left image signal L into which the 2D image signal is embedded when the judgement result of the judgement section 12 indicates the 2D connection (when one of the SD endoscope 2 and the HD endoscope 3 is connected).

The clock changing section 36 converts the clock of the image signal extracted by the L/R extraction section 35, from the image processing clock (for example, 148 MHz) to the SD clock (for example, 13.5 MHz).

The HD resolution conversion section 31 is a high definition conversion section configured to convert the resolution of the LR synthetic image signal subjected to the image processing or the 2D image signal embedded into one of the left image signal L and the right image signal R (for example, left image signal L) and subjected to the image processing, to the resolution of the high definition image signal with the image processing clock.

That is, the HD resolution conversion section 31 converts, at the image processing clock (for example, 148 MHz), the resolution of the LR synthetic image signal outputted from the image processing section 16 or the resolution of the 2D image signal embedded into the left image signal L, to the display resolution of one of the HD monitor 6 and the 3D-HD monitor 7 that are the output monitors.

Here, the LR synthetic image signal outputted from the HD resolution conversion section 31 in the 3D connection is, for example, an LR synthetic image signal in a so-called side-by-side format with 4400×1125i (frame rate: 59.94 Hz) or 5280×1125i (frame rate: 50 Hz) as shown in FIG. 3, and both the left image signal L and the right image signal R included inside are image signals with 1920×1080i.

On the other hand, the HD image signal outputted from the HD resolution conversion section 31 in the 2D connection is, for example, a progressive image signal with 1920×1080p in one of 2200×1125p (frame rate: 59.94 Hz) and 2640×1125p (frame rate: 50 Hz) as shown in FIG. 5. Here, FIG. 5 is a diagram showing an example of the HD image signal outputted from the HD resolution conversion section 31. Therefore, it is assumed in the present embodiment that the HD monitor 6 is a monitor in a progressive format (note that when the HD monitor 6 is a monitor in an interlace format, the signal is converted to an interlace image signal and outputted).

The SD resolution conversion section 32 converts the resolution of the image signal outputted from the clock changing section 36 to the display resolution of the SD monitor 5 that is the output monitor.

In this way, the clock changing section 36 and the SD resolution conversion section 32 form a standard definition conversion section configured to convert the resolution of one of the left image signal L and the right image signal R extracted by the L/R extraction section 35 or the resolution of the 2D image signal embedded into one of the left image signal L and the right image signal R (for example, left image signal L), to the resolution of the standard definition image with the clock of the standard definition image.

The HD enhancement section 33 applies an enhancement processing for HD to the HD image signal outputted from the HD resolution conversion section 31.

The SD enhancement section 34 applies an enhancement processing for SD to the SD image signal outputted from the SD resolution conversion section 32.

According to the video processor 1 with the configuration, a combination of the output from the HD enhancement section 33 and the output from the SD enhancement section 34 is "LR synthetic image signal and SD image signal" in the 3D connection and is "HD image signal and SD image signal" in the 2D connection.

Note that although it is assumed that the inputted HD image signal is, for example, 1920×1080i in the first embodiment, the outputted HD image signal is, for example, an image signal with 1920×1080p according to the configuration of the present embodiment, and 1920×1080p can also be accepted for the inputted HD image signal.

Here, when the inputted HD image signal is 1920×1080p, the input clock is 148 MHz. Therefore, the clock changing section 13 and the clock changing section 14 do not perform special clock conversion. The LR synthesis section 15 outputs the inputted HD image signal without performing special synthesis, and the image processing section 16 executes a process corresponding to the progressive image.

According to the second embodiment, substantially the same effect as that in the first embodiment can be attained. Even in the 3D connection, not only the 3D image signal, but also the SD image signal can be outputted.

As for the 2D HD image signal, an image signal with 1920×1080p can be inputted, processed, and outputted. The image quality can be further improved.

Note that although the video processor has been mainly described above, the present invention may be an activation method of video processor for activating the video processor as described above, a control program for causing a computer to execute the activation method of video processor, a computer-readable non-transitory recording medium recording the control program, or the like.

The present invention is not limited to the embodiments, and in an execution phase, the constituent elements can be modified without departing from the concept of the present invention to embody the present invention. A plurality of constituent elements disclosed in the embodiments can be appropriately combined to form various aspects of the invention. For example, some of the constituent elements illustrated in the embodiments may be removed. Constituent elements across different embodiments may also be appropriately combined. In this way, it is obvious that various modifications and applications can be made without departing from the scope of the invention.

What is claimed is:

1. A video processor comprising:
   a judgement section configured to judge whether an inputted image signal is a 3D image signal including a left image signal and a right image signal or a 2D image signal;
   an image signal synthesis section configured to embed the left image signal and the right image signal into an image signal in a side-by-side format to output the signal if the judgement section judges that the inputted image signal is the 3D image signal and configured to embed the 2D image signal into a position corresponding to one of a left image and a right image in an image signal in a side-by-side format to output the signal if the judgement section judges that the inputted image signal is the 2D image signal; and
   an image processing section configured to apply image processing to the image signal in the side-by-side format outputted by the image signal synthesis section.

2. The video processor according to claim 1, wherein the image processing section applies the image processing to the image signal in the side-by-side format at an image processing clock twice or more than twice as much as a clock of the 3D image signal.

3. The video processor according to claim 1, further comprising:
   an image signal dividing section configured to divide the image signal in the side-by-side format subjected to the image processing into the left image signal and the right image signal;
   a high definition conversion section configured to convert a resolution of the one of the left image signal and the right image signal divided by the image signal dividing section or a resolution of the 2D image signal embedded into a position corresponding to the one of the left image signal and the right image signal to a resolution of a high definition image signal such that the resolution corresponds to a high definition monitor that is an output destination; and
   a standard definition conversion section configured to convert a resolution of another of the left image signal and the right image signal divided by the image signal dividing section to the resolution of the high definition image signal such that the resolution corresponds to the high definition monitor if the judgement section judges that the inputted image signal is the 3D image signal and configured to convert the resolution of the 2D image signal embedded into the position corresponding to the one of the left image signal and the right image signal to a resolution of a standard definition image signal such that the resolution corresponds to a standard definition monitor that is an output destination if the judgement section judges that the inputted image signal is the 2D image signal.

4. The video processor according to claim 1, further comprising:
   a high definition conversion section configured to convert a resolution of the image signal in the side-by-side format subjected to the image processing or the resolution of the 2D image signal embedded into the position corresponding to the one of the left image signal and the right image signal and subjected to the image processing to the resolution of the high definition image signal such that the resolution corresponds to the high definition monitor that is the output destination;
   an image signal extraction section configured to extract the one of the left image signal and the right image signal in which the 2D image signal is embedded and subjected to the image processing if the judgement section judges that the inputted image signal is the 2D image signal; and
   a standard definition conversion section configured to convert the resolution of the 2D image signal embedded into the one of the left image signal and the right image signal to the resolution of the standard definition image signal such that the resolution corresponds to the standard definition monitor that is the output destination.

5. The video processor according to claim 4, wherein the image signal extraction section extracts the left image signal or the right image signal from the image signal in the side-by-side format subjected to the image processing if the judgement section judges that the inputted image signal is the 3D image signal, and the standard definition conversion section converts the resolution of the left image signal or the right image signal extracted by the image signal extraction section to the resolution of the standard definition image signal such that the resolution corresponds to the standard definition monitor that is the output destination.

6. An activation method of a video processor, the method comprising:
   by a judgement section, judging whether an inputted image signal is a 3D image signal including a left image signal and a right image signal or a 2D image signal;
   by an image signal synthesis section, embedding the left image signal and the right image signal into an image signal in a side-by-side format to output the signal if the judgement section judges that the inputted image signal is the 3D image signal and embedding the 2D image signal into a position corresponding to one of a left image and a right image in an image signal in a side-by-side format to output the signal if the judgement section judges that the inputted image signal is the 2D image signal; and by an image processing section, applying image processing to the image signal in the side-by-side format outputted by the image signal synthesis section.

\* \* \* \* \*